United States Patent [19]
Massiet

[11] Patent Number: 5,520,618
[45] Date of Patent: May 28, 1996

[54] FOOT CLEANER MASSAGER AND CALLUS REMOVER

[76] Inventor: Paul Massiet, 14591 Bowling Green St., Westminster, Calif. 92683

[21] Appl. No.: 150,412

[22] Filed: Nov. 9, 1993

[51] Int. Cl.⁶ .......................... A45D 29/00; A61H 35/00; A47K 7/00
[52] U.S. Cl. .................. 601/136; 132/74.5; 15/104.92
[58] Field of Search ................... 132/74.5, 76.4, 132/76.5; 119/83, 85; 601/160, 156, 158, 168, 136; 15/104.8, 104.92

[56] References Cited

U.S. PATENT DOCUMENTS

| | | | |
|---|---|---|---|
| 1,931,146 | 10/1933 | Hampel | 4/177 |
| 1,954,940 | 4/1934 | Mikel | 601/136 |
| 2,604,377 | 7/1952 | Eames | 21/61 |
| 2,735,434 | 2/1956 | De Rossett | 132/76.4 |
| 2,852,793 | 9/1958 | Shelton | 15/106 |
| 3,100,483 | 8/1963 | Altmeyer et al. | 128/25 |
| 3,253,293 | 5/1966 | George et al. | 15/215 |
| 3,283,756 | 11/1966 | Turley | 128/66 |
| 3,416,178 | 12/1968 | James | 15/104.92 |
| 3,543,747 | 12/1970 | Gustafson | 128/67 |
| 3,548,439 | 12/1970 | Berst | 15/104.92 |
| 3,577,985 | 5/1971 | Guffin | 601/136 |
| 3,885,555 | 5/1975 | Nobbs | 128/25 B |
| 3,973,286 | 8/1976 | Logan | 15/104.92 |
| 4,003,372 | 1/1977 | Willoby | 128/25 B |
| 4,377,016 | 3/1983 | Niermeijer | 15/215 |
| 4,617,917 | 10/1986 | Miller | 128/62 R |
| 4,922,859 | 5/1990 | Durell et al. | 119/83 |
| 5,158,073 | 10/1992 | Bukowski | 128/25 B |
| 5,177,829 | 1/1993 | Simpson | 15/104.92 |

FOREIGN PATENT DOCUMENTS 2266656  11/1993  United Kingdom ............ 119/83

*Primary Examiner*—John G. Weiss
*Attorney, Agent, or Firm*—Stetina Brunda & Buyan

[57] ABSTRACT

An apparatus for cleaning, massaging, and removing calluses from a foot. The apparatus includes a base with an upper platform surface, the upper platform surface has a first section having a plurality of upstanding frusto-conical protuberance of uniform height as well as a passageway through which a liquid detergent may be dispensed. The upper platform surface also has a second section having a surface to receive an abrasive material that, when rubbed by a foot, is effective in removing calluses from the foot. The apparatus may further include an enclosed reservoir containing a liquid cleaning agent that, when depressed, causes the liquid cleaning agent to pass from the reservoir and eventually onto the upper platform surface where the foot is thus cleaned. The apparatus may also have a decorative shape and be made of resilient, water-impervious material.

1 Claim, 1 Drawing Sheet

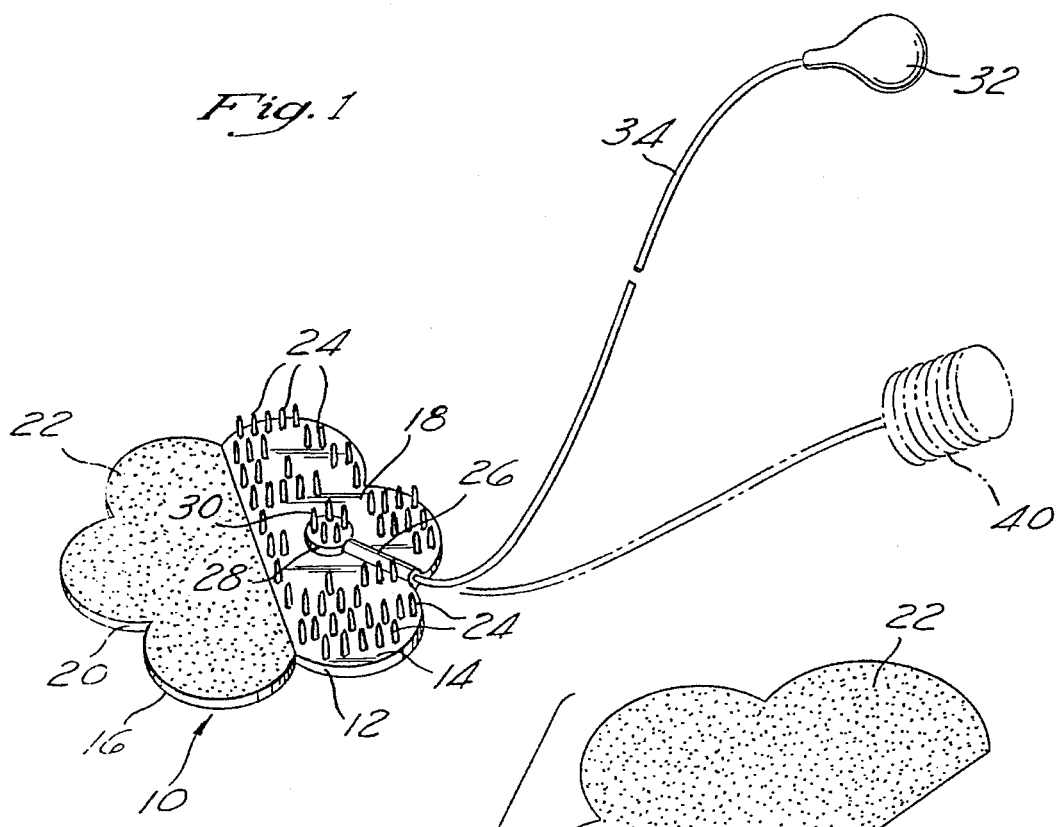
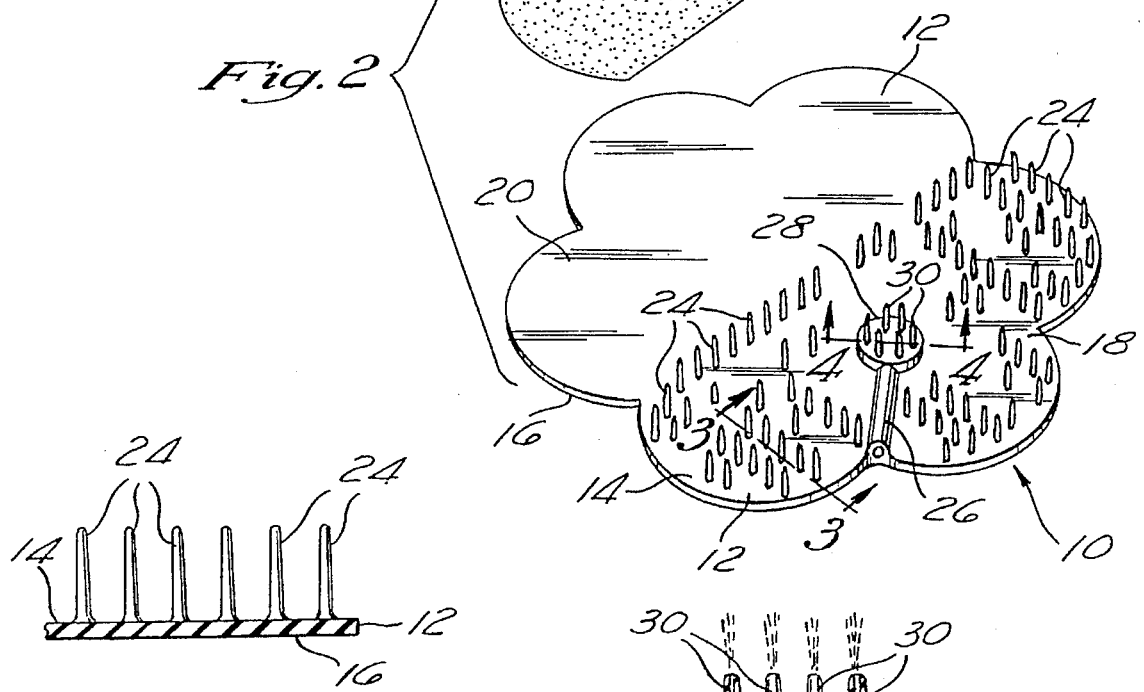
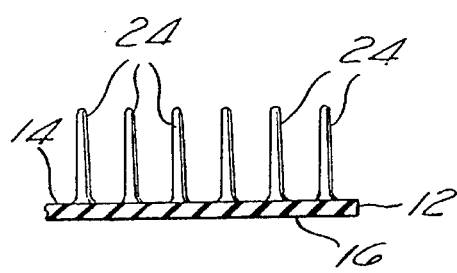
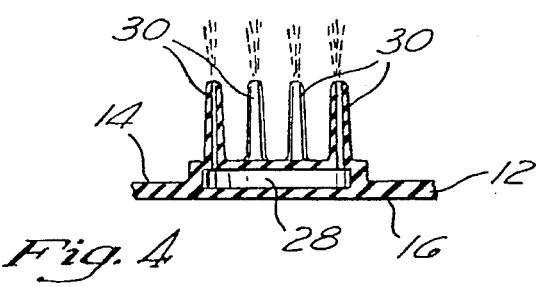

FOOT CLEANER MASSAGER AND CALLUS REMOVER

FIELD OF THE INVENTION

The present invention relates to hygienic devices, and more particularly, to devices for cleaning, massaging and removing calluses from the foot of a user.

BACKGROUND OF THE INVENTION

Foot cleaning and massaging devices are known in the art. Such massaging devices are shown, for example, in U.S. Pat. No. 3,100,483 to Altmeyer et al. and U.S. Pat. No. 3,885,555 to Nobbs, where rubberized mats having a plurality of protuberances are utilized as massaging surfaces for the feet. Likewise, U.S. Pat. No. 3,973,286 to Logan and U.S. Pat. No. 3,416,178 to James disclose foot washing devices having a series of brushes with external pumps that can be used to apply a liquid cleaning agent to the foot while the foot is being cleaned. Furthermore, U.S. Pat. No. 2,735,434 to De Rossett discloses a callus removing device whereby calluses are removed by rubbing the foot over a platform of abrasive material.

However, despite these and other numerous attempts to find an effective and efficient way of cleaning the feet, such prior art devices have generally been met with limited success. Such devices have often been considered as too ineffective or too unsightly to be utilized continuously. In addition, these devices have the drawback of not providing a sufficiently safe way of cleaning the feet as these devices normally require the person to balance on one foot while the other foot is washed.

Yet notwithstanding the lack of widespread acceptance for such devices, a substantial need exists for a hygienic foot cleaner that can be used by individuals and more particularly certain individuals who have ambulatory difficulties making them incapable of properly cleaning their feet. Such persons, because of a limited range of motion or disability, cannot properly clean their feet with traditional devices such as brushes or washcloths. Accordingly, these individuals are rarely able to clean their feet properly and, as a result, can develop numerous foot related diseases and disorders.

Because of past failures in trying to find an effective foot cleaning device, coupled with the fact that a significant non-ambulatory or ambulatory deficient population is in need of such a device, it is apparent that there is a need for a cleaning device that can safely and effectively clean, massage and remove calluses from the foot of an individual without requiring that individual to balance on one foot or exert unnecessary effort.

SUMMARY OF THE INVENTION

The present invention provides an improved foot hygiene device specifically adapted for rapidly and easily cleaning, massaging and removing calluses from the feet. The foot hygiene device of the present invention comprises a base with a lower surface and an upper platform surface, with the upper platform surface being preferably divided into two sections. Both sections provide a surface adapted to receive a foot of a user with the first section having a plurality of frusto-conical shaped protuberances preferably of uniform length that, when rubbed across in a to and fro manner by the foot, provides a means of massaging the feet. The base further has one or more passageways and basin disposed therein through which a liquid cleaning agent is dispensed onto the first section of the upper platformed surface. The cleaning agent is discharged onto the upper platform surface through means of one or more hollow protuberances extending upwardly from the basin. The second section of the upper platform surface is preferably generally flat and is designed to receive a panel having an abrasive upper surface. The panel is releasably affixed to the flat second section so that the abrasive surface is oriented in an upward direction and thereby dispensed to selectively contact portions of a users foot to remove calluses therefrom.

In a preferred embodiment, an external, enclosed reservoir with a tube extending therefrom is attached to the passageway disposed within the base so that a liquid cleaning agent may be controllably dispensed at a rate desired by the user. This external reservoir may be in the form of a collapsible bellow or a compressible bulb that, when manually depressed, forces the liquid cleaning agent from the reservoir, through the tube and base, and eventually onto the first section of the platform surface. By simultaneously dispensing the cleaning agent and moving the foot over the plurality of protuberances, the feet become thoroughly cleansed. In addition, the rubbing motion of the feet over the protuberances produces a pleasurable massaging experience for the feet.

It is therefore an object of the present invention to provide a foot hygiene device which can safely and effectively clean the feet of a user and simultaneously massage the feet of the user without requiring the user to bend over or exert unnecessary effort.

Another object of the present invention is to provide a foot hygiene device which can effectively remove calluses from the feet by simply brushing the feet over a portion of the device.

Another object of the present invention is to provide a foot hygiene device that is resilient, flexible, and impervious to water.

Yet another object of the present invention is to provide a foot hygiene device which is decorative in design and is easy to use.

BRIEF DESCRIPTION OF THE DRAWINGS

FIG. 1 is a perspective view of a foot hygiene device according to a preferred embodiment of the present invention.

FIG. 2 is a perspective view of the foot hygiene device showing a detached abrasive surface to be placed upon a portion of the upper platform surface.

FIG. 3 is a cross-sectional view taken along line 3—3 of FIG. 2 illustrating a portion of the base with a row of protuberances extending upwardly with respect to the base.

FIG. 4 is cross-sectional view taken along line 4—4 of FIG. 2 illustrating a portion of the base, passageway and basin disposed therein, and a plurality of hollow frusto-conical protuberance used to dispense a liquid cleaning agent.

DETAILED DESCRIPTION OF THE PREFERRED EMBODIMENT

Referring to the drawings, and particularly to FIGS. 1 and 2, there is shown a foot hygiene device 10 embodying the principles of the present invention. The device comprises a generally flat base 12 preferably formed of a non-slip rubber or polymer material adapted to be placed in a shower stall or bathtub (not shown) having an upper platform surface 14 and a lower bottom surface 16.

The upper platform surface 14, is preferably segregated into a first section 18 and second section 20 as shown. The first section 18 has a plurality of upstanding preferably frusto-conical shaped protuberances 24 of generally equal length, a section of which being more clearly depicted in FIG. 3. This first section 18 also includes one ore more passageway 26 running through a portion of the base 12 and having a central basin 28. Extending upwardly from the central basin 28 is a plurality of hollow frusto-conical protuberances 30. FIG. 4 more clearly illustrates this basin and hollow protuberance arrangement.

With reference to FIG. 1, an external, enclosed reservoir 32 for holding liquid cleaning agent and a tube 34 extending therefrom are shown. The external reservoir 32 is connected to the base by the tube 34 that allows for the passage of the liquid cleaning agent from the reservoir 32 through the tube 34, through the base passageway 26 and basin 28, and onto the upper platform surface 14 by means of the hollow frusto-conical protuberances 30. The liquid cleaning agent is dispensed upon the upper platform surface 14 by means of compressing the reservoir 32 by a respective one of a person's hand or a person's foot, wherein the reservoir 32 may take the form of a compressible bulb, as illustrated, or a collapsible bellow 40, as depicted in FIG. 1, or other type of dispensing pump mechanism. A tube 34 that is shorter in length may be incorporated when the reservoir 32 is specifically designed to be compressed by a foot.

The second section 20 of the upper platform surface 14 is generally flat and is shaped and designed to receive a panel of abrasive material 22. The panel of abrasive material 22 is preferably formed of a silica or pumice impregnated paper material and is disposed with the abrasive material facing upwardly. Furthermore, the panel of abrasive material 22 may be releasably attachable to the second section 20 as by way of adhesive or frictional engagement so as to allow for replacement of the abrasive panel 22 as the panel becomes warn with use.

Referring to FIG. 2, the panel of abrasive material 22 and the upper platform surface 14 of the base 12 are shown, with the panel of abrasive material 22 being disengaged from the second section 20 of the upper platform surface 14. In use, the panel of abrasive material 22 is securely fastened upon the surface of the second section 20 whereby the surface of abrasive material 22 provides means for removing calluses from the feet.

Referring to FIG. 3, a plurality of frusto-conical protuberances 24 are shown. The protuberances 24 are of generally equal length, with a preferred length being approximately 1 inch. Furthermore, the protuberances 24 may by uniformly distributed or randomly distributed throughout the entire surface area of section 18.

Referring to FIG. 4, a cross-sectional view of the base 12, basin 28, and hollow frusto-conical protuberances 30 are shown. As mentioned above, these hollow protuberances 30 allow for the passage of a liquid cleaning agent from the passageway 26 and basin 28 and ultimately the upper platform surface. As a result the user may controllably dispense the amount of cleaning agent necessary to insure proper cleansing of the feet.

The device is particularly well suited for use in both bathtubs and shower stalls where the user can utilize the present invention as part of the showering or bathing experience. To insure greater reliability when used for this purpose, the lower surface 16 of the base 12 may be provided with a rough irregular surface configuration which resists slippage relative the bathtub or shower stall.

Furthermore, the hygiene device of the present invention may be shaped in numerous decorative designs, such as a flower as shown in FIGS. 1 and 2, and may further come in an assortment of colors or ornamental patterns so as to be permanently dispensed within a shower stall or bathtub and be aesthetically pleasing.

In using the present invention, a user may place the base 12 within a bathtub or shower stall. Subsequently, the user may stand or alternative sit upon the edge of the bathtub thereby supporting the users weight thereon and may simultaneously massage and cleanse his or her feet in an effective and efficient manner by merely shuffling his or her feet back and forth over the first section 18 of protuberances 24 of the upper platform surface 14. Likewise, by compressing the reservoir 32 containing the liquid cleaning agent, user may controllably apply the amount of cleaning agent desired. In addition, by merely placing the users feet upon the second section 20 of the upper platform surface 14, the user may then effectively and efficiently remove any calluses on the feet by again shuffling his or her feet across the abrasive surface 22 attached to the second section 20. In sum, the user is able to thoroughly clean and massage his or her feet as well as be able to remove any calluses that are present on the feet by means of simply using the present invention.

Thus, the apparatus of the present invention, with various preferred embodiments thereof, have been described in detail with the various advantages being set forth. It is understood, however, that equivalents are possible and that variations in structure may be made that fall within the underlying principles of the present invention.

What is claimed is:

1. An apparatus for cleaning, massaging, and removing calluses from a foot or pair of feet comprising:

a) a base with a lower surface and an upper platform surface, the base having at least one passage way and basin disposed therein for holding and transferring a liquid cleaning agent;

b) the upper platform surface having a first and second section;

c) the first section of the upper platform surface having a plurality of upstanding frusto-conical protuberances, wherein at least one of the protuberances has a duct, the duct being shaped and oriented to permit discharge of the liquid cleaning agent from the basin onto the upper platform surface;

d) the second section having a generally flat surface being shaped and designed to releasably secure a panel having an abrasive upper surface, the abrasive upper surface being suited to cause the removal of the calluses when the foot is rubbed across the surface; and e) wherein said apparatus is fabricated from resilient, water-impervious material, said lower surface being shaped and designed to secure the apparatus in a substantially stationary position while in use.

\* \* \* \* \*